(12) United States Patent
Takagi et al.

(10) Patent No.: US 7,790,290 B2
(45) Date of Patent: Sep. 7, 2010

(54) INTERMEDIATE FILM OF LAMINATED SAFETY GLASS WITH ANTIGLARE FUNCTION AND NOVEL NEODYMIUM COMPOUND

(75) Inventors: Shunji Takagi, Fukui (JP); Yoshiharu Fujio, Hyogo (JP)

(73) Assignee: Hopnic Laboratory Co., Ltd., Sabae-shi (JP)

( * ) Notice: Subject to any disclaimer, the term of this patent is extended or adjusted under 35 U.S.C. 154(b) by 426 days.

(21) Appl. No.: 11/814,243

(22) PCT Filed: Jan. 18, 2006

(86) PCT No.: PCT/JP2006/300643

§ 371 (c)(1),
(2), (4) Date: Jul. 18, 2007

(87) PCT Pub. No.: WO2006/077884

PCT Pub. Date: Jul. 27, 2006

(65) Prior Publication Data

US 2009/0202844 A1  Aug. 13, 2009

(30) Foreign Application Priority Data

Jan. 18, 2005  (JP)  ............................. 2005-010133

(51) Int. Cl.
*B32B 17/10* (2006.01)
*C08K 5/098* (2006.01)

(52) U.S. Cl. ................. 428/437; 428/436; 524/301; 524/398; 534/16
(58) Field of Classification Search ................. 428/436, 428/437; 524/301, 398; 534/16
See application file for complete search history.

(56) References Cited

U.S. PATENT DOCUMENTS

| 4,504,616 A | 3/1985 | Uehara et al. ............... 524/398 |
| 4,559,372 A | 12/1985 | Giroud-Abel ............... 523/205 |
| 5,610,114 A | 3/1997 | Robert et al. ............... 502/115 |

FOREIGN PATENT DOCUMENTS

| EP | 0 549 808 A1 | 7/1993 |
| JP | 58-160941 | 9/1983 |
| JP | 5 202109 | 8/1993 |
| JP | 2000 347024 | 12/2000 |
| JP | 2004-123424 | 4/2004 |
| JP | 2004 226913 | 8/2004 |
| WO | WO 04/000549 A1 | 12/2003 |

*Primary Examiner*—D. S Nakarani
(74) *Attorney, Agent, or Firm*—Oblon, Spivak, McClelland, Maier & Neustadt, L.L.P.

(57) ABSTRACT

The present invention provides an intermediate film for use in laminated glass, comprising a resin composition containing polyvinyl butyral, a plasticizer and a neodymium compound having compatibility in both the plasticizer and a plasticized resin, where the neodymium compound is a neodymium salt of a polyvalent ester of a dicarboxylic or polycarboxylic acid wherein one carboxyl group is not esterified. The intermediate film is useful in producing a laminated glass.

12 Claims, 1 Drawing Sheet

INTERMEDIATE FILM OF LAMINATED SAFETY GLASS WITH ANTIGLARE FUNCTION AND NOVEL NEODYMIUM COMPOUND

TECHNICAL FIELD

The present invention relates generally to an intermediate film for use in transparent laminated safety glass having selective light absorption and a production method thereof, and more specifically relates to an intermediate film for use in laminated safety glass comprising neodymium (III) blended into a plasticized polyvinyl butyral. Furthermore, the present invention relates to a novel neodymium compound preferable for use in the production of the above intermediate film and a production method thereof.

BACKGROUND ART

Laminated glass having an intermediate film consisting of a thermoplastic resin such as polyvinyl butyral sandwiched between a pair of glass panels is often used as glass for automobiles or construction materials such as for front doors. While such laminated glass is safe because shards of glass will not be scattered even upon receiving an impact from an external source, its high transparency can pose a problem, for example, when used as the glass for an automobile, since sunlight, illumination or the headlights of oncoming cars can cause glare in the driver's eyes.

As methods of preventing glare in such laminated glass, there are methods of reducing the light using colored glass or colored intermediate films. However, when applying these light reducing methods to automobile glass, the anti-glare effect is achieved, but this can be accompanied by reduced visibility at night due to the reduced light, thus actually increasing the risk.

In order to solve these problems, the glare due to rays of the sun or reflection from the road surface is often prevented by providing a colored strip on the top portion or bottom portion of an automobile's windshield (Patent Document 1). For example, Patent Document 1 describes that an aesthetic effect and an anti-glare effect against reflections from the road surface particularly during the day can be achieved by providing a colored strip containing an organic or inorganic pigment at the bottom portion of the windshield (paragraph 0008). However, the central portion of the windshield which takes up almost the entire field of view of the driver is left transparent, so that the anti-glare effect cannot be achieved, in particular, for the headlights of oncoming cars at night.

Patent Document 1: JP 2004-23424A

DISCLOSURE OF THE INVENTION

Problems to be Solved by the Invention

The present invention has the purpose of offering an intermediate film for laminated glass and laminated glass using said intermediate film, which solves the problems of laminated glass using conventional polyvinyl butyral resins as the intermediate film, appearing the same as uncolored, transparent laminated glass even at nighttime, and capable of providing an anti-glare effect against the headlights of oncoming cars at nighttime when used for the glass in automobiles.

Furthermore, the present invention has the purpose of offering a novel neodymium compound suitable for use in the production of the above-described intermediate film, and a method of production thereof.

Means for Solving the Problems

As means for solving the above problems, the present inventors focused on the spectral absorption properties of neodymium (III) compounds, and performed diligent research toward mixing and dissolving neodymium (III) compounds into intermediate films containing polyvinyl butyral, thereby achieving the present invention.

In accordance therewith, in a first embodiment, the present invention relates to an intermediate film for use in laminated glass containing a resin composition containing polyvinyl butyral, a plasticizer and a neodymium compound having compatibility in a plasticized resin.

Here, the neodymium compound is preferably a neodymium salt of a polyvalent ester monocarboxylic acid, and more preferably represented by the following formula (1):

$$[(R_1OCO)_xR_2COO]_m(R_3COO)_nNd \qquad (1)$$

wherein $R_1$ represents an alkyl group or an aryl group, $R_2$ represents an alkylene group or an arylene group, $R_3$ represents a saturated or unsaturated alkyl group or aryl group, or a $(R'_1OCO)_xR'_2$ group (where $R'_1$ and $R'_2$ are defined the same as $R_1$ and $R_2$ except that $R_1 \neq R'_1$ and $R_2 \neq R'_2$), x is an integer from 1-3, and m is a positive number satisfying the relationship $0 < m < 3$, and n is a number satisfying the relationship $m+n=3$. Additionally, the neodymium salt of a polyvalent ester monocarboxylic acid is preferably a neodymium salt of at least two polyvalent ester monocarboxylic acids. Furthermore, the above resin composition preferably contains 100 parts by weight of polyvinyl butyral, 20-100 parts by weight of the plasticizer and 1-40 parts by weight of the neodymium salt of a polyvalent ester monocarboxylic acid.

Furthermore, the present invention relates to a laminated glass formed by sandwiching an intermediate film as described above between a pair of glass panels.

In a second embodiment, the present invention relates to a novel neodymium salt of a polyvalent ester monocarboxylic acid represented by the following formula (1):

$$[(R_1OCO)_xR_2COO]_m(R_3COO)_nNd \qquad (1)$$

wherein $R_1$ represents an alkyl group or an aryl group, $R_2$ represents an alkylene group or an arylene group, $R_3$ represents a saturated or unsaturated alkyl group or aryl group, or a $(R'_1OCO)_xR'_2$ group (where $R'_1$ and $R'_2$ are defined the same as $R_1$ and $R_2$ except that $R_1 \neq R'_1$ and $R'_2 \neq R'_2$), x is an integer from 1-3, and m is a positive number satisfying the relationship $0 < m < 3$, and n is a number satisfying the relationship $m+n=3$.

In a third embodiment, the present invention relates to a neodymium salt of a polyvalent ester monocarboxylic acid characterized by being obtained by mixing at least one polyvalent ester monocarboxylic acid or a neodymium salt thereof expressed by the following Formula (2):

$$(R_1OCO)_xR_2COOH \qquad (2)$$

wherein $R_1$ represents an alkyl group or an aryl group, $R_2$ represents an alkylene group or an arylene group and x is an integer of 1-3; and at least one aliphatic or aromatic monocarboxylic acid or a neodymium salt thereof, or at least one polyvalent ester monocarboxylic acid or a neodymium salt thereof expressed by the following Formula (3):

$$R_3COOH \quad (3)$$

wherein $R_3$ represents a saturated or unsaturated alkyl group or aryl group, or a $(R'_1OCO)_xR'_2$ group where $R'_1$ and $R'_2$ are defined the same as $R_1$ and $R_2$ except that $R_1 \neq R'_1$ and $R_2 \neq R'_2$; or when mixing carboxylic acids of the above Formulas (2) and (3), further mixing in a neodymium compound and allowing to react.

Here, in one embodiment, $R_3$ is not a $(R'_1OCO)_xR'_2$ group and in another embodiment, $R_1$ is a $(R'_1OCO)_xR'_2$ group.

In a fourth embodiment, the present invention relates to a method of producing a neodymium salt of a polyvalent ester monocarboxylic acid, characterized by mixing at least one polyvalent ester monocarboxylic acid or a neodymium salt thereof expressed by the following Formula (2):

$$(R_1OCO)_xR_2COOH \quad (2)$$

wherein $R_1$ represents an alkyl group or an aryl group, $R_2$ represents an alkylene group or an arylene group and x is an integer of 1-3; and at least one aliphatic or aromatic monocarboxylic acid or a neodymium salt thereof, or at least one polyvalent ester monocarboxylic acid or a neodymium salt thereof expressed by the following Formula (3):

$$R_3COOH \quad (3)$$

wherein $R_3$ represents a saturated or unsaturated alkyl group or aryl group, or a $(R'_1OCO)_xR'_2$ group where $R'_1$ and $R'_2$ are defined the same as $R_1$ and $R_2$ except that $R_1 \neq R'_1$ and $R_2 \neq R'_2$; or when mixing carboxylic acids of the above Formulas (2) and (3), further mixing in a neodymium compound and allowing to react.

Here, in one embodiment, $R_3$ is not a $(R'_1OCO)_xR'_2$ group and in another embodiment, $R_3$ is a $(R'_1OCO)_xR'_2$ group.

BEST MODES FOR CARRYING OUT THE INVENTION

Neodymium (III) compounds have the property of selectively absorbing light in the vicinity of wavelength 580 nm which is the red-green boundary wavelength region and the vicinity of wavelength 525 nm which is the green-blue boundary wavelength region, and optical materials containing dissolved neodymium (III) compounds are known to have an anti-glare effect on the human eye. That is, optical materials containing dissolved neodymium (III) compounds reduce glare in bright areas by absorbing light in the vicinity of yellow to which humans have high visual sensitivity, and have high visual sensitivity to colors, i.e. causing colors to appear sharp by absorbing light in the boundary wavelength regions between red, green and blue, the three primary colors of light, as a result of which the glare from the headlights of oncoming cars can be reduced even in dark areas, while enabling sharp vision even while reducing light at specific wavelengths based on the above principles.

Acrylic panels with evenly dispersed neodymium have been produced by providing neodymium (III) compounds having optical properties in transparent acrylic resin beads (e.g., JP 2551690B, JP H4-72347A). The methods described in these publications involve producing acrylic resin beads containing neodymium by dissolving neodymium salts of carboxylic acid together with acrylic monomers in a solvent and inducing suspension polymerization or the like.

Conventionally, neodymium is blended with acrylic resins by using inorganic or organic salts of neodymium. Specific examples of inorganic salts include neodymium oxide, neodymium hydroxide and neodymium nitrate, and specific examples of organic salts include fatty acid salts such as neodymium acrylate, neodymium methacrylate, neodymium acetate, neodymium propionate, neodymium butyrate, neodymium isobutyrate, neodymium valerate, neodymium isovalerate, neodymium n-octanoate and neodymium 2-ethylhexanoate, and aromatic monocarboxylic acid salts such as neodymium benzoate.

On the other hand, as described above, plasticized resins having a plasticizer blended with a resin such as polyvinyl butyral are normally used in the intermediate films for laminated glass in automobiles or the like. Generally, about 40 parts by weight of a plasticizer are blended with 100 parts by weight of polyvinyl butyral. However, upon confirmation by the present inventors, most of the publicly known neodymium compounds (salts) including those listed above did not dissolve into plasticized polyvinyl butyral resin at all. Furthermore, while neodymium nitrate was observed to dissolve to some extent, it was not practicable for having the drawbacks that the heat applied during sheet formation or adhesive formation caused the resulting mixture to turn from yellow to brown, or the color of light to change as a laminated glass. Therefore, no intermediate films comprising neodymium compounds blended with plasticized polyvinyl butyral are known.

Thus, in the present invention, new neodymium compounds compatible with plasticized polyvinyl butyral have been synthesized, and by mixing these with plasticized resins, the present inventors succeeded in obtaining a new intermediate film for use in laminated glass having an exceptional anti-glare effect.

In the present invention, the novel neodymium compound compatible with plasticized polyvinyl butyral is preferably a neodymium salt of a polyvalent ester monocarboxylic acid.

For the purposes of the present specification, "polyvalent ester monocarboxylic acid" refers to a carboxylic acid having at least one ester group in its molecule. Specific examples include monoesters of aliphatic dicarboxylic acids such as oxalic acid, malonic acid, succinic acid, glutaric acid, adipic acid and sebacic acid, monoesters of aromatic dicarboxylic acids such as phthalic acid, isophthalic acid and terephthalic acid, and diesters of tricarboxylic acids such as tricarballylic acid and trimellitic acid, but the compound is not limited to these examples.

In the present invention, compounds expressed by the following Formula (1) are preferred among the above-described neodymium salts of a polyvalent ester monocarboxylic acid.

$$[(R_1OCO)_xR_2COO]_m(R_3COO)_n Nd \quad (1)$$

In the above Formula (1):

$R_1$ represents generally a $C_1$-$C_{12}$, preferably a $C_1$-$C_{10}$, more preferably a $C_1$-$C_8$ alkyl group or aryl group. Specific examples include straight or branched alkyl groups such as methyl, ethyl, propyl, isopropyl, butyl, isobutyl, pentyl, isopentyl, hexyl, isohexyl, heptyl and octyl, and aryl groups such as phenyl and benzyl.

$R_2$ represents generally a $C_1$-$C_{12}$, preferably a $C_1$-$C_{10}$, more preferably a $C_1$-$C_8$ alkylene group or arylene group, for example, straight or branched alkylene groups such as methylene, ethylene, butylenes, pentylene, hexylene, heptylene or octylene, and arylene groups such as phenylene.

$R_3$ represents generally a $C_1$-$C_{12}$, preferably a $C_1$-$C_{10}$, more preferably a $C_1$-$C_8$ saturated or unsaturated alkyl group or aryl group, or a $(R'_1OCO)_xR'_2$ group (where $R'_1$ and $R'_2$ are defined the same as $R_1$ and $R_2$ except that $R_1 \neq R'_1$ and $R_2 \neq R'_2$).

x is an integer from 1-3, preferably 1 or 2.

m is a positive number less than or equal to 3, and n is a number satisfying the relationship m+n=3.

Here, when $R_1$ is a $(R'_1OCO)_xR'_2$ group, the neodymium salt of a polyvalent ester monocarboxylic acid of the above Formula (1) is a neodymium salt including at least two types of polyvalent ester monocarboxylic acids.

On the other hand, if $R'_1$ is other than a $(R'_1OCO)_xR'_2$ group in the above Formula (1), then these compounds correspond to mixed neodymium salts of at least one type of polyvalent ester monocarboxylic acid and at least one aliphatic or aromatic monocarboxylic acid.

In the present specification, "mixed neodymium salt" shall refer to a neodymium salt of at least one type of polyvalent ester monocarboxylic acid and at least one type of aliphatic or aromatic monocarboxylic acid.

Examples of aliphatic or aromatic monocarboxylic acids forming mixed salts include aliphatic monocarboxylic acids such as acrylic acid, methacrylic acid, acetic acid, propionic acid, butyric acid, isobutyric acid, valeric acid, isovaleric acid, n-octanoic acid and 2-ethylhexanoic acid, and aromatic monocarboxylic acids such as benzoic acid.

When x is 2 or 3 in the above Formula (1), in other words, if the salt has at least two ester groups ($R_1OCO$—), the $R_1$, groups of the residues may be the same or different. Additionally, the neodymium salt of the present invention may be a mixture of a plurality of compounds represented by the above Formula (1). Therefore, m and n in the above Formula (1) are defined as average values. The ratio of the polyvalent ester monocarboxylate residue (($R_1OCO)_xR_2COO$—) and the aliphatic or aromatic monocarboxylate residue ($R_3COO$—), i.e. the range of m and n in Formula (1) is not particularly limited as long as they satisfy the relationship m+n=3

Neodymium salts wherein R— is a $(R'_1OCO)_xR'_2$ group in the above Formula (1) (neodymium salts containing only at least two types of polyvalent ester monocarboxylic acids) can be synthesized, for example, by mixing at least two polyvalent ester monocarboxylic acids, forming a triethylamine salt thereof, then stirring to mix said triethylamine salt and neodymium nitrate in a non-aqueous solvent such as ethanol, or by separately preparing triethylamine salts at least two polyvalent ester carboxylic acids, forming neodymium salts thereof, then mixing the resulting neodymium salts in a solvent or a plasticizer.

On the other hand, mixed neodymium salts of a polyvalent ester monocarboxylic acid and an aliphatic or aromatic monocarboxylic acid can be synthesized by the methods indicated below.

(1) Mixing an acid mixture of a polyvalent ester monocarboxylic acid and an aliphatic or aromatic monocarboxylic acid with a neodymium compound such as neodymium oxide to induce a direct reaction, and purifying by removing the excess acid by a method such as crystallization.

(2) Mixing a neodymium salt of a polyvalent ester monocarboxylic acid and a neodymium salt of an aliphatic or aromatic monocarboxylic acid in a solvent to induce an acid residue exchange reaction. It is efficient to use a plasticizer used for an intermediate film of a polyvinyl butyral resin for use in laminated safety glass as the medium in the acid exchange, because this obviates the need for purification after the acid exchange.

(3) Dissolving a neodymium salt of an aliphatic or aromatic monocarboxylic acid in a liquid polyvalent ester monocarboxylic acid to induce an acid residue exchange reaction, then purifying by removing the excess acid and free acids by a method such as crystallization.

(4) Forming a mixture of a polyvalent ester monocarboxylic acid and an aliphatic or aromatic monocarboxylic acid into an amine salt, then stirring neodymium nitrate or neodymium chloride in a non-aqueous solvent such as ethanol to induce a reaction, then purifying by removing the nitric acid salts or hydrochloric acid salts of amines that are formed as byproducts by rinsing or the like.

The present inventors looked to the chemical structures of the plasticizers used in the intermediate films of laminated glass consisting of polyvinyl butyral resins and the like, in particular; by synthesizing new neodymium salts of organic acids having an ester group and studying their solubility in plasticized resins, thus achieving the present invention. However the novel neodymium salts of the present invention also dissolve well in tricresyl phosphates which do not have a carboxylic acid ester structure. That is the solubility of the neodymium salts of the present invention is not due to a simple structural similarity between its polyvalent ester monocarboxylic acids and plasticizers, but rather can be inferred to also involve an interaction between the neodymium salts and the plasticizer or resin.

The polyvinyl butyral used in the present invention is obtained by butyralating polyvinyl alcohol with butyraldehyde. The above polyvinyl alcohol is usually obtained by saponification of polyvinyl acetate, where a polyvinyl alcohol with a saponification of 80-99.8 mol % is normally used. Additionally, while there is no particular limitation on the molecular weight and molecular weight distribution of the polyvinyl butyral resin used in the present invention, a resin with a degree of polymerization of 500 to 2000 is used as the polyvinyl alcohol resin to form the raw material, in view of the moldability and physical properties. Additionally, the degree of butyralation of the polyvinyl butyral used in the present invention is usually 40-85%, preferably 50-75%.

The plasticizer used in the present invention may be any that is normally used to plasticize polyvinyl butyral, examples of which include triethylene glycol di-2-ethylhexanoate, triethylene glycol di-caprylate, triethylene glycol di-2-ethyl-butylate, triethylene glycol dihexanoate, triethylene glycol di-n-heptanoate, dibutylphthalate, benzylbutylphthalate, butylphthalylbutylglycolate and tricresyl phosphate. These plasticizers may be used singly or in a combination of a plurality thereof, and normally about 40 parts by weight should be added for every 100 parts of polyvinyl butyral.

The intermediate film for laminated glass according to the present invention can be produced, preferably by dissolving and mixing together a neodymium salt of a polyvalent ester monocarboxylic acid expressed by the above Formula (1), a resin consisting of polyvinyl butyral and a plasticizer of said resin, kneading while optionally heating, and forming into a sheet, for example.

The intermediate film of laminated glass of the present invention preferably consists of 100 parts by weight of polyvinyl butyral, 20-100 parts by weight of a plasticizer, and 1-40 parts by weight of a neodymium compound solubilized in the mixture thereof.

A laminated safety glass can be produced by sandwiching the intermediate film of the present invention between two glass panels and securing, then preferably heating under reduced pressure and gradually cooling. A laminated glass produced by using the intermediate film of the present invention retains the advantageous effects of polyvinyl butyral resin such as impact resistance, while also being transparent and having exceptional anti-glare functions based on the selective light absorption properties of the neodymium (III) compound.

In the present invention, the neodymium salt of a polyvalent ester monocarboxylic acid is preferably a compound expressed by the following Formula (1):

$$[(R_1OCO)_xR_2COO]_m(R_3COO)_nNd \qquad (1)$$

(wherein:

$R_1$ represents an alkyl group or aryl group, $R_2$ represents an alkylene group or arylene group, $R_3$ represents a saturated or unsaturated alkyl group or aryl group, or a $(R'_1OCO)_xR'_2$ group (where $R'_1$ and $R'_2$ are defined the same as $R_1$ and $R_2$ except that $R_1 \ne R'_1$ and $R_2 \ne R'_2$), x is an integer from 1-3, m is a positive number satisfying the relationship 0<m<3, and n is a number satisfying the relationship m+n=3).

Additionally, in the present invention, the neodymium salt of a polyvalent ester monocarboxylic acid can be obtained by mixing at least one polyvalent ester monocarboxylic acid or a neodymium salt thereof expressed by the following Formula (2):

$$(R_1OCO)_xR_2COOH \qquad (2)$$

{wherein:

$R_1$ represents an alkyl group or an aryl group, $R_2$ represents an alkylene group or an arylene group and x is an integer of 1-3}; and at least one aliphatic or aromatic monocarboxylic acid or a neodymium salt thereof, or at least one polyvalent ester monocarboxylic acid or a neodymium salt thereof expressed by the following Formula (3):

$$R_3COOH \qquad (3)$$

{wherein:

$R_3$ represents a saturated or unsaturated alkyl group or aryl group, or a $(R'_1OCO)_xR'_2$ group where $R'_1$, and $R'_2$ are defined the same as $R_1$ and $R_2$ except that $R_1 \ne R'_1$ and $R_2 \ne R'_2$}; or when mixing carboxylic acids of the above Formulas (2) and (3), further mixing in a neodymium compound and allowing to react.

Furthermore, in the present invention, the neodymium salt of a polyvalent ester monocarboxylic acid can be obtained by mixing at least one polyvalent ester monocarboxylic acid or a neodymium salt thereof expressed by the following Formula (2):

$$(R_1OCO)_xR_2COOH \qquad (2)$$

{wherein:

$R_1$ represents an alkyl group or an aryl group, $R_2$ represents an alkylene group or an arylene group and x is an integer of 1-3}; and at least one aliphatic or aromatic monocarboxylic acid or a neodymium salt thereof, or at lest one polyvalent ester monocarboxylic acid or a neodymium salt thereof expressed by the following Formula (3):

$$R_3COOH \qquad (3)$$

{wherein:

$R_3$ represents a saturated or unsaturated alkyl group or aryl group, or a $(R'_1OCO)_xR'_2$ group where $R'_1$ and $R'_2$ are defined the same as $R_1$ and $R_2$ except that $R_1 \ne R'_1$ and $R_2 \ne R'_2$; or when mixing carboxylic acids of the above Formulas (2) and (3), further mixing in a neodymium compound and allowing to react.

In the above Formulas (1), (2) and (3), $R_1$ represents generally a $C_1$-$C_{12}$, preferably a $C_1$-$C_{10}$, more preferably a $C_1$-$C_8$ alkyl group or aryl group. Specific examples include straight or branched alkyl groups such as methyl, ethyl, propyl, isopropyl, butyl, isobutyl, pentyl, isopentyl, hexyl, isohexyl, heptyl and octyl, and aryl groups such as phenyl and benzyl. $R_2$ represents generally a $C_1$-$C_{12}$, preferably a $C_1$-$C_{10}$, more preferably a $C_1$-$C_8$ alkylene group or arylene group, for example, straight or branched alkylene groups such as methylene, ethylene, butylenes, pentylene, hexylene, heptylene or octylene, and arylene groups such as phenylene. $R_3$ represents generally a $C_1$-$C_{12}$, preferably a $C_1$-$C_{10}$, more preferably a $C_1$-$C_8$ saturated or unsaturated alkyl group or aryl group, or a $(R'_1OCO)_xR'_2$ group (where $R'_1$ and $R'_2$ are defined the same as $R_1$ and $R_2$ except that $R_1 \ne R'_1$ and $R_2 \ne R'_2$). x is an integer from 1-3, preferably 1 or 2. m is a positive number less than or equal to 3, and n is a number satisfying the relationship m+n=3

Here, when $R_3$ is a $(R'_1OCO)_xR'_2$ group, the neodymium salt of a polyvalent ester monocarboxylic acid of the above Formula (1) or the neodymium salt of a polyvalent ester monocarboxylic acid obtained from the above Formulas (2) and (3) is a neodymium salt including at least two types of polyvalent ester monocarboxylic acids, while on the other hand, when $R_3$ is other than a $(R'_1OCO)_xR'_2$ group, then these compounds correspond to mixed neodymium salts of at least one type of polyvalent ester monocarboxylic acid and at least one aliphatic or aromatic monocarboxylic acid.

When x is 2 or 3 in the above formulas, in other words, if the salt has at least two ester groups ($R_1OCO$—), the $R_1$ groups of the residues may be the same or different. Additionally, the neodymium salt of the present invention may be a mixture of a plurality of compounds represented by the above Formula. Therefore, m and n in the above Formula (1) are defined as average values. The ratio of the polyvalent ester monocarboxylate residue ($(R_1OCO)_xR_2COO$—) and the aliphatic or aromatic monocarboxylate residue ($R_3COO$—), i.e. the range of m and n in Formula (1) is not particularly limited as long as they satisfy the relationship m+n=3.

Neodymium salts wherein $R_3$ is a $(R'_1OCO)_xR'_2$ group in the above Formula (1) or (3) (neodymium salts containing only at least two types of polyvalent ester monocarboxylic acids) can be synthesized, for example, by mixing at least two polyvalent ester monocarboxylic acids, forming a triethylamine salt thereof, then stirring to mix said triethylamine salt and neodymium nitrate in a non-aqueous solvent such as ethanol, or by separately preparing triethylamine salts at least two polyvalent ester carboxylic acids, forming neodymium salts thereof, then mixing the resulting neodymium salts in a solvent or a plasticizer.

On the other hand, mixed neodymium salts of a polyvalent ester monocarboxylic acid and an aliphatic or aromatic monocarboxylic acid can be synthesized by the methods indicated below.

(1) Mixing an acid mixture of a polyvalent ester monocarboxylic acid and an aliphatic or aromatic monocarboxylic acid with a neodymium compound such as neodymium oxide to induce a direct reaction, and purifying by removing the excess acid by a method such as crystallization.

(2) Mixing a neodymium salt of a polyvalent ester monocarboxylic acid and a neodymium salt of an aliphatic or aromatic monocarboxylic acid in a solvent to induce an acid residue exchange reaction.

(3) Dissolving a neodymium salt of an aliphatic or aromatic monocarboxylic acid in a liquid polyvalent ester monocarboxylic acid to induce an acid residue exchange reaction, then purifying by removing the excess acid and free acids by a method such as crystallization.

(4) Forming a mixture of a polyvalent ester monocarboxylic acid and an aliphatic or aromatic monocarboxylic acid into an amine salt, then stirring neodymium nitrate or neodymium chloride in a non-aqueous solvent such as ethanol to induce a reaction, then purifying by removing the nitric acid salts or hydrochloric acid salts of amines that are formed as byproducts by rinsing or the like.

Examples of aliphatic or aromatic monocarboxylic acids include aliphatic monocarboxylic acids such as acrylic acid, methacrylic acid, acetic acid, propionic acid, butyric acid, isobutyric acid, valeric acid, isovaleric acid, n-octanoic acid and 2-ethylhexanoic acid, and aromatic monocarboxylic acids such as benzoic acid.

Examples of neodymium salts of aliphatic or aromatic monocarboxylic acids include neodymium salts of isobutyric acid, neodymium salts of phenoxyacetic acid, neodymium salts of 4-(t-butyl)benzoic acid and neodymium salts of 2-methoxybenzoic acid.

Examples of polyvalent monocarboxylic acids include monoesters of aliphatic dicarboxylic acids such as oxalic acid, malonic acid, succinic acid, glutaric acid, adipic acid and sebacic acid, monoesters of aromatic dicarboxylic acids such as phthalic acid, isophthalic acid and terephthalic acid, and diesters of tricarboxylic acids such as tricarballylic acid and trimellitic acid.

Examples of neodymium salts of a polyvalent ester monocarboxylic acid include neodymium salts of phthalic acid mono(isobutyl)ester, neodymium salts of phthalic acid mono (n-butyl)ester, neodymium salts of phthalic acid (mono(2-phenoxyethyl)ester and neodymium salts of phthalic acid mono(n-butoxyethyl) ester.

EXAMPLES

The present invention shall be explained in further detail by means of the below examples. The data $^1$H-NMR data given in the synthesis examples are values measured at a resonance frequency of 270 MHz, with the sample in a solution of deuterated dimethylsulfoxide (DMSO-d6) or heavy water. ppm: parts per million; s: single line; d: double line; t: triple line; m: multiple line.

Synthesis Example 1

Synthesis of Neodymium Salt of Monoisobutylphthalic Acid 1-1. Synthesis of Monoisobutylphthalic Acid 148.2 g of anhydrous phthalic acid and the molar equivalent 74.2 g of isobutyl alcohol were added to a 500 ml glass round-bottomed flask equipped with stirring blades, thermometer and Dimroth condenser, heated while slowly stirring, and after the generated heat at about 80° C. wore off, raised to a temperature of 140° C., which was maintained for 2 hours. The mixture was subsequently cooled to 60° C. The acid value (number of mg of KOH necessary to neutralize 1 g of a sample) of the reaction solution was 257.5. Since the acid value for the case where the reaction is 100% complete is 252.4, the reaction rate was computed to be 98%.

$^1$H-NMR data (DMSO-d6 solvent): 0.94 ppm (6H, d), 1.97 ppm (1H, m), 4.01 ppm (2H, d), 7.65 ppm (3H/phenylene group, m) and 7.74 ppm (1H/phenylene group, m).

1-2. Synthesis of Neodymium Salt

The monoisobutylphthalic acid obtained in 1-1 was formed into a triethylamine salt in anhydrous ethanol, after which an ethanol solution of neodymium nitrate was added while stirring. That is, a reactor similar to that of 1-1 was used to stir a solution obtained by adding 30 ml of an anhydrous ethanol to 70.0 g of the monoisobutylphthalic acid obtained in 1-1, while dripping 30.4 g of triethylamine while maintaining at 20° C. by cooling in an ice water bath. After dripping, the solution was heated for 30 minutes at 40° C. to prepare a synthesis solution of monoisobutylphthalic acid-triethylamine salts. Next, this synthesis solution was adjusted to 20° C., and a solution obtained by dissolving 43.8 g of neodymium nitrate into 100 ml of ethanol was dripped in while stirring. After dripping, the solution was heated to 40° C. for 30 minutes, to produce a synthesis solution of a neodymium salt of monoisobutylphthalic acid. Then, ethanol was distilled from this synthesis solution to concentrate, 150 ml of chloroform and 200 ml of water were added to the concentrate and stirred, and the resulting neodymium salt of monoisobutylphthalic acid was extracted and washed. After further washing this chloroform solution with water twice, it was transferred to a 2 L cylindrical separable flask, and 800 ml of hexane were slowly added while stirring to crystallize. Crystals obtained by filtering this slurry solution, then further the filtered crystals were added to 400 ml of hexane, stirred and washed, then refiltered, and the crystals were dried under reduced pressure at 50° C., to obtain 68.1 g of a neodymium salt of monoisobutylphthalic acid (yield 84%).

$^1$H-NMR data (DMSO-d6 solvent): 0.67 ppm (6H, d), 1.68 ppm (1H, m), 3.90 ppm (2H, d), 7.77 ppm (2H/phenylene group; m) 7.91 ppm (1H/phenylene group, broad s) and 9.24 ppm (1H/phenylene group, broad s).

Elemental Analysis ($C_{36}H_{39}O_{12}Nd$; Fw=807.8): C: hypothetical value 53.37/measured value 53.01; H: hypothetical value 4.87/measured value 4.77.

Synthesis Example 2

Synthesis of Neodymium Salt of Isobutyric Acid 80.0 g of neodymium oxide and 251.0 g of isobutyric acid were added to a TL glass round-bottomed flask equipped with stirring blades, thermometer and Dimroth condenser, heated to 100° C. while stirring to induce a reaction, thus synthesizing neodymium isobutyrate. 2 hours after heat generation began, the reaction solution became transparent, at which point it was cooled. After cooling to 40° C., 800 ml of methanol were slowly added, and the generated neodymium isobutyrate was crystallized. This slurry solution was filtered, the precipitated neodymium isobutyrate was separated out, this cake was washed twice with 500 ml of methanol, then dried under reduced pressure at 50° C. to obtain 189.0 g of a neodymium isobutyrate salt (yield: 98%).

$^1$H-NMR data (heavy water solvent): 1.58 ppm (6H, d) and 3.74 ppm (1H, broad s).

Elemental Analysis ($C_{12}H_{21}O_6Nd$; Fw=405.5): C: hypothetical value 35.54/measured value 34.65; H: hypothetical value 5.22/measured value 5.21.

Synthesis Example 3

Synthesis Example (1) of Mixed Neodymium Salt of Monoisobutylphthalic Acid-Isobutyric Acid The neodymium salt of monoisobutylphthalic acid described in the above Synthesis Example 1 and the neodymium isobutyrate described in Synthesis Example 2 were mixed together in an organic solvent for synthesis.

4.00 g (4.95 mmol) of a neodymium salt of monoisobutylphthalic acid and 1.00 g (2.47 mmol) of neodymium isobutyrate were added to 20.00 g of dichloromethane in a 50 ml screw bottle, and the solution was stirred using a magnetic stirrer, whereupon the clouding due to the slurry of neodymium salt powder gradually thinned, and complete dissolution was achieved after 20 minutes. On the other hand, slurry solutions of each alone, that is, a mixture of 4.00 g of a neodymium salt of monoisobutylphthalic acid in 20.00 g of dichloromethane, and a mixture of 1.00 g of neodymium isobutyrate in 20.00 g of dichloromethane were such that even after 8 hours of stirring, the clouding remained much the same as when the stirring was started. These phenomena suggest that the neodymium salt mixture of Synthesis Example 3 undergoes acid residue exchange in dichloromethane, forming a mixed salt wherein the average m value in the following chemical formula is 2 corresponding to the molar ratio of materials used, which salt then dissolves.

$(CH_3CH(CH_3)CH_2OCO\Phi COO)m(CH_3CH(CH_3)COO)nNd$ (wherein Φ represents a phenylene group)

This dichloromethane solution was concentrated, then vacuum-dried at 50° C. to remove the dichloromethane. 0.5 g of a neodymium salt thus obtained was added to 2.0 g of triethylene glycol di-2-ethylhexanoate and heated to 60° C. upon which it easily dissolved. On the other hand, 0.4 g of a neodymium salt of monoisobutylphthalic acid were added to 2.0 g of triethylene glycol di-2-ethylhexanoate and heated to 60° C., but was left mostly undissolved. Additionally, 0.1 g of neodymium isobutyrate was added to 2.0 g of triethylene glycol di-2-ethylhexanoate and heated to 60° C., but was left mostly undissolved.

Synthesis Example 4

Synthesis Example (2) of Mixed Neodymium Salt of Monoisobutylphthalic Acid-Isobutyric Acid Neodymium isobutyrate was dissolved in monoisobutylphthalic acid, to synthesize a mixed neodymium salt by means of acid residue exchange.

Using a glass reactor like that of Synthesis Example 1, 133.0 g of the monoisobutylphthalic acid described in Synthesis Example 1-1 was heated to 70° C. while stirring, then 81.1 g of the neodymium isobutyrate described in Synthesis Example 2 were added a little at a time and mixed. After completing the addition, most of the neodymium isobutyrate was dissolved, but there were some undissolved lumps, so the solution was raised to a temperature of 90° C. over 1 hour, to completely dissolve. After cooling to 25° C., 200 ml of hexane were added to this synthesis solution, this solution was transferred to a 1 L cylindrical separable flask, and 600 ml of hexane were added a little at a time while stirring, thus precipitating a neodymium salt. The stirring was stopped, and the precipitated neodymium salts were allowed to settle, then the supernatant fluid was decanted and discarded. Next, 600 ml of hexane were added, heated to 65° C., and stirred for 30 minutes to extract the remaining monoisobutylphthalic acid and isobutyric acid. Then, the solution was cooled to 25° C., the supernatant fluid was decanted and discarded, 600 ml of hexane were added once again and a similar operation was performed to remove the remaining monoisobutylphthalic acid and isobutyric acid. The neodymium salts obtained in this way were vacuum-dried at 50° C. to obtain 114 g of neodymium salts. On the other hand, upon performing gas chromatography of the supernatant fluid and quantitative analysis of the isobutyric acid, the average m value of the neodymium salt in the above chemical formula was found to be 1.9 (from m=1.9, the yield of the neodymium-<salt was calculated to be 86%).

5.00 g of the mixed neodymium salt of monoisobutylphthalic acid-isobutyric acid prepared in the above Synthesis Example 4 were added to 20.00 g of triethylene glycol di-2-ethylhexanoate and heated to 60° C. while stirring, whereupon it quickly dissolved to form a uniform transparent solution.

Synthesis Example 5

Synthesis of Neodymium Salt of Mono-n-butylphthalic Acid

The compound was synthesized by a method similar to that of Synthesis Example 1 described above.

5-1. Synthesis of Mono-n-butylphthalic Acid 148.2 g of anhydrous phthalic acid and 1.05 times the molar equivalent 77.8 g of n-butyl alcohol were added to a 500 ml glass round-bottomed flask equipped with stirring blades, thermometer and Dimroth condenser, heated while slowly stirring, and after the generated heat at about 90° C. wore off, raised to a temperature of 130° C., which was maintained for 2 hours. The mixture was subsequently cooled to 60° C. The acid value (number of mg of KOH necessary to neutralize 1 g of a sample) of the reaction solution was 253.8.

Since the acid value for the case where the reaction is 100% complete is 248.4, the reaction rate was computed to be 98%.

5-2. Synthesis of Neodymium Salt

The mono-n-butylphthalic acid obtained in 5-1 was formed into a triethylamine salt in anhydrous ethanol, after which an ethanol solution of neodymium nitrate was added while stirring. That is, a reactor similar to the above was used to stir a solution obtained by adding 30 ml of an anhydrous ethanol to 68.1 g of the mono-n-butylphthalic acid obtained in 5-1, while dripping 30.4 g of triethylamine while maintaining at 30° C. or less by cooling in an ice water bath. After dripping, the solution was heated for 30 minutes at 40° C. to prepare a synthesis solution of mono-n-butylphthalic acid-triethylamine salt. Next, this synthesis solution was adjusted to 20° C., and a solution obtained by dissolving 43.8 g of neodymium nitrate into 100 ml of ethanol was dripped in while stirring. After dripping, the solution was heated to 40° C. for 30 minutes, to produce a synthesis solution of a neodymium salt of mono-n-butylphthalic acid. Then, ethanol was distilled from this synthesis solution to concentrate, 150 ml of chloroform and 200 ml of water were added to the concentrate and stirred, and the resulting neodymium salt of mono-n-butylphthalic acid was extracted and washed. After further washing this chloroform solution with, water twice, the chloroform was distilled out. The solid obtained by distillation was crushed, then dried under reduced pressure at 50° C. to obtain 72.9 g of a neodymium salt of mono-n-butylphthalic acid (yield 90%).

$^1$H-NMR data (DMSO-d6 solvent): 0.69 ppm (3H/methyl group of n-butyl group, t), 1.14 ppm (2H/methylene group of n-butyl group, m), 1.33 ppm (2H/methylene group of n-butyl group, broad s), 4.10 ppm (2H/methylene group of n-butyl group, m), 7.79 ppm (2H/phenylene group, m), 7.90 ppm (1H/phenylene group, broad s) and 9.19 ppm (1H/phenylene group, broad s).

Elemental Analysis ($C_{36}H_{39}O_{12}Nd$; Fw=807.8): C: hypothetical value 53.27/measured value 53.13; H: hypothetical value 4.87/measured value 4.87.

Synthesis Example 6

Synthesis of Neodymium Salt of Mono(2-phenoxyethyl)phthalic Acid

The compound was synthesized by a method similar to that of Synthesis Example 1 described above.

6-1. Synthesis of Mono(2-phenoxyethyl)phthalic Acid 148.1 g of anhydrous phthalic acid and roughly the molar equivalent 139.3 g of 2-phenoxyethanol were added to a 500 ml glass round-bottomed flask equipped with stirring blades, thermometer and Dimroth condenser, heated while slowly stirring, and after the generated heat at about 90° C. wore off, raised to a temperature of 130° C., which was maintained for 1 hour. The mixture was subsequently cooled to 60° C. The acid value (number of mg of KOH necessary to neutralize 1 g of a sample) of the reaction solution was 212.6. Since the acid value for the case where the reaction is 100% complete is 202.2, the reaction rate was computed to be 95%.

6-2. Synthesis of Neodymium Salt

The mono(2-phenoxyethyl)phthalic acid obtained in 6-1 was formed into a triethylamine salt in anhydrous ethanol, after which an ethanol solution of neodymium nitrate was added while stirring. That is, a reactor similar to the above was used to stir a solution obtained by adding 30 ml of an anhydrous ethanol to 88.6 g of the mono(2-phenoxyethyl) phthalic acid obtained in 6-1, while dripping 30.4 g of triethylamine while maintaining at 30° C. or less by cooling in an ice water bath. After dripping, the solution was heated for 30 minutes at 40° C. to prepare a synthesis solution of mono(2-phenoxyethyl)phthalic acid-triethylamine salts. Next, this synthesis solution was adjusted to 20° C., and a solution obtained by dissolving, 43.8 g of neodymium nitrate into 100 ml of ethanol was dripped in while stirring. After dripping, the solution was heated to 40° C. for 2 hours, to produce a synthesis solution of a neodymium salt of mono(2-phenoxyethyl)phthalic acid. Then, ethanol was distilled from this synthesis solution to concentrate, 300 ml of dichloromethane were added to the concentrate to form a solution, this solution was transferred to a 1 L separating funnel, shaken after pouring 400 ml of water into this separating funnel, and the resulting neodymium salts of mono(2-phenoxyethyl)phthalic acid were washed. After further washing this dichloromethane solution twice with 400 ml of water, the dichloromethane was distilled out. The solid obtained by distillation was crushed, then dried under reduced pressure at 50° C. to obtain 94.0 g of a neodymium salt of mono(2-phenoxyethyl)phthalic acid (yield 94%).

$^1$H-NMR data (DMSO-d6 solvent): 3.66 ppm (2H/ethylene group, broad s), 4.39 ppm (2H/ethylene group, broad s), 6.59 ppm (2H/phenyl group of phenoxy, d), 6.82 ppm (1H/phenyl group of phenoxy, t), 7.12 ppm (2H/phenyl group of phenoxy, t), 7.79-7.86 ppm (3H/phenylene group of phthalic acid, m) and 8.91 ppm (1H/phenylene group of phthalic acid, broad s).

Elemental Analysis ($C_{48}H_{39}O_{15}Nd$; Fw=1000.1): C: hypothetical value 57.64/measured value 57.46; H: hypothetical value 3.93/measured value 4.16.

Synthesis Example 7

Synthesis of Neodymium Salt of Phenoxyacetic Acid

The compound was synthesized by the same method as that for Synthesis Example 1-2 above, that is, after forming a triethylamine salt of phenoxyacetic acid in anhydrous methanol, a methanol solution of neodymium nitrate was added while stirring. Specifically, a reactor similar to that of 1-1 was used to stir a solution obtained by adding 100 ml of an anhydrous methanol to 45.65 g (0.3 mol) of phenoxyacetic acid, while dripping 30.4 g (0.3 mol) of triethylamine while maintaining at 25° C. by cooling in an ice water bath. After dripping, the solution was heated for 30 minutes at 40° C. to prepare a transparent synthesis solution of phenoxyacetic acid-triethylamine salts. Next, this synthesis solution was maintained at about 30° C., and a solution obtained by dissolving 43.8 g of neodymium nitrate into 100 ml of methanol was dripped in while stirring. Upon completion of the dripping of the neodymium nitrate solution, it began to cloud, and the clouding increased with time. 30 minutes after completion of dripping, the solution was heated to 40° C. for 30 minutes, to produce a slurry solution of a neodymium salt of phenoxyacetic acid. Crystals obtained by filtering this slurry solution were added to 200 ml of methanol, stirred and washed, then refiltered, and 200 ml of methanol were once again added to the crystals, stirred and washed, then filtered. The resulting crystals were dried under reduced pressure at 50° C., to obtain 38.8 g of a neodymium salt of phenoxyacetic acid (yield 65%).

$^1$H-NMR data (DMSO-d6 solvent): 5.30 ppm (2H/acetyl group, broad s), 6.93 ppm (1H/phenyl group, broad s) and 7.29 ppm (4H/phenyl group, broad s, overlap of two types of H).

Elemental Analysis ($C_{24}H_{21}O_9Nd$; Fw=597.7): C: hypothetical value 48.22/measured value 46.53; H: hypothetical value 3.54/measured value 3.79.

Synthesis Example 8

Synthesis of Neodymium Salt of 4-t-butylbenzoic Acid

The compound was synthesized by the same method as that for Synthesis Example 1-2 above, that is, after forming a triethylamine salt of 4-tertiary-butylbenzoic acid in anhydrous methanol, a methanol solution of neodymium nitrate was added while stirring. Specifically, a reactor similar to that of 1-1 was used to stir a slurry solution obtained by adding 100 ml of an anhydrous methanol to 53.48 g (0.3 mol) of 4-tertiary-butylbenzoic acid, while dripping 30.4 g (0.3 mol) of triethylamine while maintaining at 30° C. by cooling in an ice water bath. After dripping, the solution was heated for 30 minutes at 40° C. to prepare a transparent synthesis solution of 4-tertiary-butylbenzoic acid-triethylamine salts. Next, 200 ml of methanol were further added to this synthesis solution and maintained at about 30° C., and a solution obtained by dissolving 43.8 g of neodymium nitrate into 100 ml of methanol was dripped in while stirring. Upon dripping of about half of the neodymium nitrate solution, it began to cloud, upon completion of dripping, a high-concentration slurry solution was obtained. After completion of dripping, the solution was heated to 40° C. for 30 minutes, to produce a slurry solution of a neodymium salt of 4-tertiary-butylbenzoic acid. Crystals obtained by filtering this slurry solution were added to 400 ml of methanol, stirred and washed, then refiltered, and 400 ml of methanol were once again added to the crystals stirred and washed, then filtered. The resulting crystals were dried under reduced pressure at 50° C., to obtain 59.3 g of a neodymium salt of 4-tertiary-butylbenzoic acid (yield 88%

$^1$H-NMR data (DMSO-d6 solvent): 1.53 ppm (9H/methyl group, s), 8.04 ppm (2H/phenylene group, broad s) and 9.55 ppm (2H/phenylene group, broad s).

Element Analysis ($C_{33}H_{39}O_6Nd$; Fw=675.9): C: hypothetical value 58.64/measured value 58.28; H: hypothetical value 5.82/measured value 5.78.

Synthesis Example 9

Synthesis of Neodymium Salt of 2-methoxybenzoic Acid

The compound was synthesized by the same method as that for Synthesis Example 1-2 above, that is, after forming a triethylamine salt of 2-methoxybenzoic acid in anhydrous ethanol, an ethanol solution of neodymium nitrate was added while stirring. Specifically, a reactor similar to that of 1-1 was used to stir a slurry solution obtained by adding 100 ml of an anhydrous ethanol to 45.65 g (0.3 mol) of 2-methoxybenzoic acid, while dripping 30.4 g (0.3 mol) of triethylamine while maintaining at 20-30° C. by cooling in an ice water bath. After dripping about one-third of the triethylamine, the slurry disappeared and became transparent. After dripping, the solution was heated for 30 minutes at 40° C. to prepare a transparent synthesis solution of 2-methoxybenzoic acid-triethylamine salts. Next, while stirring this synthesis solution and holding at 25° C., a solution obtained by dissolving 43.8 g of neodymium nitrate into 120 ml of ethanol was dripped in. Upon completion of dripping, the solution was heated to 40° C., began to cloud after 40 minutes, and the clouding increased with time. After another 20 minutes, it became an extremely thick slurry solution, so 100 ml of ethanol were further added, and the solution was stirred for another hour at 40° C., then cooled to end the reaction. Next, crystals obtained by filtering this slurry solution were added to 200 ml of methanol, stirred and washed, then refiltered, and 200 ml of methanol were once again added to the crystals, stirred and washed, then filtered. The resulting crystals were dried under reduced pressure at 50° C., to obtain 50.83 g of a neodymium salt of 2-methoxybenzoic acid (yield 85%).

$^1$H-NMR data (DMSO-d6 solvent): 4.09 ppm (3H/methoxy group, s), 7.52 ppm (2H/phenylene group, broad s), 7.76 ppm (1H/phenylene group, broad s) and 9.55 ppm (1H/phenylene group, broad s).

Elemental Analysis ($C_{24}H_{21}O_9Nd$; Fw=597.7): C: hypothetical value 48.22/measured value 47.63; H: hypothetical value 3.54/measured value 3.61.

Synthesis Example 10

Synthesis of Neodymium Salt of Mono(2-butoxyethyl)phthalic Acid

The compound was synthesized by a method similar to that of Synthesis Example 1 described above.

10-1. Synthesis of Mono(2-butoxyethyl)phthalic Acid 148.1 of anhydrous phthalic acid and the molar equivalent 118.2 n of 2-butoxyethanol were added to a 500 ml glass round-bottomed flask equipped with stirring blades, thermometer and Dimroth condenser, heated while slowly stirring, and after the generated heat at about 90° C. wore off, raised to a temperature of 130° C., which was maintained for 1 hour. The mixture was subsequently cooled to 60° C. The acid value (number of mg of KOH necessary to neutralize 1 g of a sample) of the reaction solution was 226.0. Since the acid value for the case where the reaction is 100% complete is 210.7, the reaction rate was computed to be 93%.

10-2. Synthesis of Neodymium Salt

The mono(2-butoxyethyl)phthalic acid obtained in 10-1 was formed into a triethylamine salt in anhydrous ethanol, after which an ethanol solution of neodymium nitrate was added while stirring. That is, a reactor similar to the above was used to stir a solution obtained by adding 50 ml of an anhydrous ethanol to 79.9 g of the mono(2-butoxyethyl)phthalic acid obtained in 10-1, while dripping 30.4 g of triethylamine while maintaining at 25° C. or less by cooling in an ice water bath. After dripping, the solution was heated for 1 hour at 40° C. to prepare a synthesis solution of mono(2-butoxyethyl)phthalic acid-triethylamine salts. Next, this synthesis solution was adjusted to 20° C., and a solution obtained by dissolving 43.8 g of neodymium nitrate into 120 ml of ethanol was dripped in while stirring. After dripping, the solution was heated to 40° C. for 1 hour, to produce a synthesis solution of a neodymium salt of mono(2-butoxyethyl)phthalic acid. Then, ethanol was distilled from this synthesis solution to concentrate, 200 ml of dichloromethane were added to the concentrate to form a solution, this solution was transferred to a 1 L separating funnel, shaken after pouring 400 ml of water into this separating funnel, and the resulting neodymium salts of mono(2-butoxyethyl)phthalic acid were washed. After further washing this chloromethane solution twice with 400 ml of water, the dichloromethane was distilled out. The solid obtained by distillation was crushed, then dried under reduced pressure at 50° C. to obtain 78.1 g of a neodymium salt of mono(2-butoxyethyl)phthalic acid (yield 83%).

$^1$H-NMR data (DMSO-d6 solvent): 0.79 ppm (3H/methyl group of n-butoxy group, m), 1.20 ppm (2H/methylene group of n-butoxy group n, m), 1.30 ppm (2H/methylene group of n-butoxy group, m), 3.14 ppm (4H/ethyl group, overlap of two types of H), 4.18 ppm (2H/methylene group of n-butoxy group, s), 7.77 ppm (2H/phenylene group, m), 7.89 ppm (1H/phenylene group; broad s, partially overlapping with 7.77 ppm), 9.02 ppm (1H/phenylene group, broad s).

Elemental Analysis ($C_{42}H_{51}O_{15}Nd$; Fw=940.1): C: hypothetical value 53.66/measured value 52.67; H: hypothetical value 5.47/measured value 5.57.

The solubility of each of the neodymium salts of Synthesis Examples 5-10 in triethylene glycol-di-2-ethylhexanoate was studied, whereupon the neodymium salts of Synthesis Examples 5-9 mostly did not dissolve, but the neodymium salt of Synthesis Example 10 was found to dissolve.

Dissolution Example 1

Dissolution of Mixed Neodymium Salts of Monoisobutylphthalic Acid-Isobutyric Acid 20.00 g of triethylene glycol di-2-ethylhexanoate were added and mixed into 25.00 g of the dichloromethane solution of neodymium salts prepared in the above Synthesis Example 3, to obtain a uniform transparent liquid. This solution was heated in a water bath with temperature adjusted to 50° C. and the dichloromethane was distilled out in a reduced pressure state using a rotary evaporator. First, the dichloromethane was roughly removed at −0.06 MPa, the distillate was discarded, then the reduced pressure state was raised gradually from −0.07 MPa to −0.10 MPa, to distill out the dichloromethane until the weight loss ended. This solution with the dichloromethane removed was a uniform transparent liquid. The results are shown in Table 1.

Comparative Dissolution Example 1

20.00 g of triethylene glycol di-2-ethylhexanoate were added to a slurry solution obtained by mixing 4.00 g of the neodymium salt of monoisobutylphthalic acid described in Synthesis Example 3 into 20.00 g of dichloromethane, then heated to 60° C. and subjected to a reflux for 1 hour, but the solution did not become a transparent liquid. Further, a rotary evaporator was used to distill the dichloromethane from the slurry solution as with the above Dissolution Example 1, but it remained cloudy and did not become transparent. The results are shown in Table 1.

Comparative Dissolution Example 2

20.00 g of triethylene glycol d—2-ethylhexanoate were added to a slurry solution obtained by mixing 1.00 g of the neodymium isobutyrate described in Synthesis Example 3 into 20.00 g of dichloromethane, then heated to 60° C. and subjected to a reflux for 1 hour, but the solution did not become a transparent liquid. Further, a rotary evaporator was used to distill the dichloromethane from the slurry solution as with the above Dissolution Example 1, but it remained cloudy and did not become transparent. The results are shown in Table 1.

Dissolution Examples 2-4

Dissolution of Mixed Neodymium Salts of Monoisobutylphthalic Acid-Isobutyric Acid (2)

The dichloromethane solutions shown in Table 1 were prepared in the same manner as in the above Synthesis Example 3, to synthesize three types of mixed neodymium salts of monoisobutylphthalic acid isobutyric acid with different values for m in the chemical formula. Next, 20.00 g of triethylene glycol di-2-ethylhexanoate were added and mixed with these synthesized solutions as with Dissolution Example 1. All three of these mixed solutions were transparent liquids. Furthermore, dichloromethane was distilled from these mixed solutions as with Dissolution Example 1. Of these three, when m=0.5, the solution was clouded, and when let stand, a precipitate of poor fluidity separated out, while the supernatant liquid at the top was a pale violet color. The other two types were uniform transparent solutions of a dark violet color like Dissolution Example 1. The results of the above are shown in Table 1.

TABLE 1

Dissolution of Mixed Neodymium Salts of Monoisobutylphthalic Acid - Isobutyric Acid
$(CH_3CH(CH_3)CH_2OCO\Phi COO)m(CH_3CH(CH_3)COO)nNd$;
$\Phi$ denotes a phenylene group

|  | Co Ex 1 | Dis Ex 2 | Dis Ex 1 | Dis Ex 3 | Dis Ex 4 | Co Ex 2 |
|---|---|---|---|---|---|---|
| Average m | 3 | 2.5 | 2 | 1 | 0.5 | 0 |
| Average n | 0 | 0.5 | 1 | 2 | 2.5 | 3 |
| Solubility [1] |  |  |  |  |  |  |
| DCM [1] | x | ○ | ○ | ○ | ○ | x |
| 3GO [1] | x | ○ | ○ | ○ | x | x |
| Content (units: g) |  |  |  |  |  |  |
| NIBP [2] | 4.00 | 5.00 | 4.00 | 2.00 | 1.00 | — |
| NIBA [2] | — | 0.50 | 1.00 | 2.00 | 2.50 | 1.00 |
| DCM | 20.00 | 20.00 | 20.00 | 20.00 | 20.00 | 20.00 |
| 3GO | 20.00 | 20.00 | 20.00 | 20.00 | 20.00 | 20.00 |
| Nd salt: mmol [3] | 6.19 | 7.43 | 7.42 | 7.41 | 7.40 | 2.47 |
| Nd salt: phm [4] | 20 | 27.5 | 25 | 20 | 17.5 | 5 |

(Note)
[1] Solubility: ○ . . . complete dissolution, x . . . not completely dissolved (some undissolved parts. DCM: dichloromethane. 3GO: triethylene glycol bis(2-ethylhexanoate). Solubility in 3GO represents the condition after distillation of DCM.
[2] NIBP: neodymium monoisobutylphthalate. Theoretical formula weight is 807.8. NIBA: neodymium isobutyrate. Theoretical formula weight is 405.5
[3] Nd salt: mmol gives the total number of moles of NIBP and NIBA. units: millimoles.
[4] Nd salt: phm represents the weight ratio of the total weight of the Nd salt when taking the weight of 3GO to be 100.

Example 1

1-1. Preparation of Intermediate Film 15 parts by weight of the mixed neodymium salt of Synthesis Example 3 were dissolved into 40 parts by weight of triethylene glycol di-2-ethylhexanoate, and this solution was mixed with 100 parts by weight of polyvinyl butyral "BH-3" (Sekisui Chemical, average degree polymerization 1700, hydroxyl groups about 34 mol %, butyralation about 65 mol %). Next, this mixture was kneaded for 5 minutes using a two-roll mill heated to 115° C., then cut into sheets to cool by radiation. These sheets were further compression molded for 10 minutes in a press heated to 130° C. via a 1 mm thick spacer, then compressed and cooled with a water-cooled press, to obtain transparent plasticized polyvinyl butyral resin sheets with a thickness of about 1 mm.

1-2. Preparation of Laminated Glass

A set of an intermediate film such as described above sandwiched between two 60 mm×60 mm glass panels of thickness 1.3 mm and clamped with a clip in two opposing directions was placed in a vacuum oven, where the air was removed at room temperature, heated to 130° C. in a vacuum, and this state held for 30 minutes, after which air was entered to return to standard pressure and gradually cool, thus resulting in a laminated glass. The laminated glass was a blue-violet transparent material.

Comparative Example 1

A laminated glass was prepared in the same manner as in Example 1 aside from the fact that the neodymium salt was not dissolved, and 40 parts by weight of triethylene glycol di-2-ethylhexanoate (3GO) were simply mixed with 100 parts by weight of polyvinyl butyral "BH-3". This laminated glass was a colorless transparent material.

Figure 1:
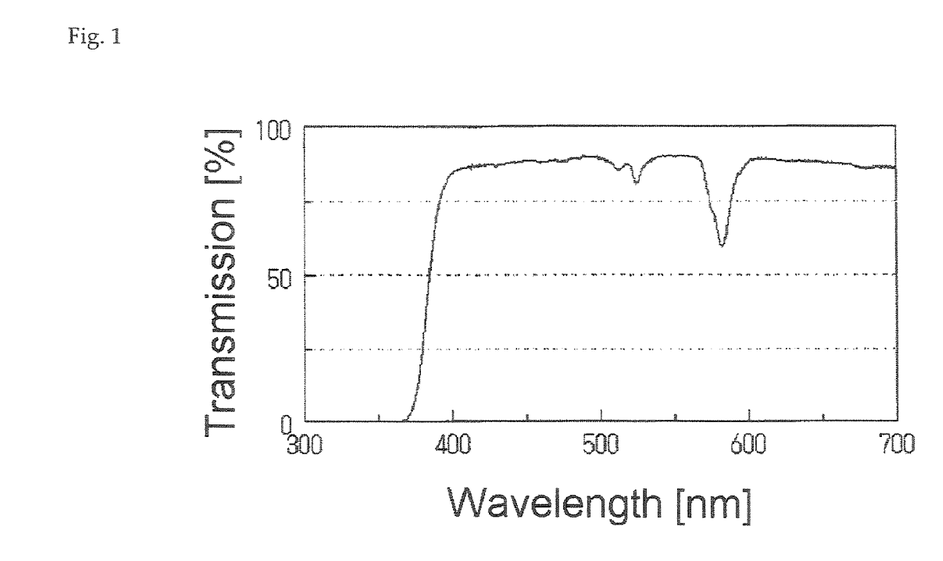
FIG. 1 is a drawing showing the visible-UV spectrum of laminated glass prepared using intermediate film of the present invention prepared in Example 1.
Figure 2:
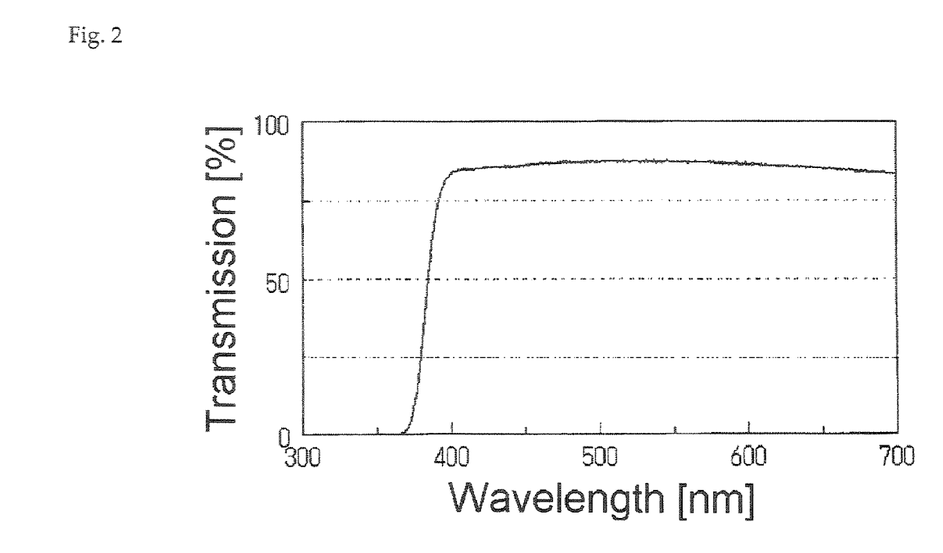
FIG. 2 is a drawing showing the visible-UV spectrum of laminated glass prepared using intermediate glass not containing a neodymium salt prepared in Comparative Example 1.

Visible-UV spectra for the laminated glass prepared in Example 1 and Comparative Example 1 when measured on the direction of lamination are shown respectively in FIGS. 1 and 2. With the laminated glass of Example 1 using the intermediate film of the present invention containing neodymium salts, a major absorption peak is visible in the vicinity of 583 nm, but such absorption was not observed with the laminated glass of Comparative Example 1.

Example 2

A laminated glass was prepared in the same manner as Example 1, using dibutylphthalate (DBP) as the plasticizer.

Example 3

A laminated glass was prepared in the same manner as Example 1, using benzylbutylphthalate (BBP) as the plasticizer. This laminated glass was a transparent material of the same tone as Example 1.

Example 4

A laminated glass was prepared in the same manner as Example 1, using tricresyl phosphate (TCP) as the plasticizer. This laminated glass was a transparent material of the same tone as Example 1, and the visible-UV spectrum was mostly the same as Example 1

The visible-UV spectra for the laminated glass prepared in the above Examples 1-4 was roughly the same as that of Example 1 shown in FIG. 1. The sizes of the main absorption peak (wavelength 583 nm) in these spectra are shown in the following Table 2 together with that of Comparative Example 1. In Table 1, the average transmission in the area where the transmission begins to fall in the vicinity of the main peak, i.e. the average value for the transmission at wavelengths of 603 nm and 567 nm was used as the base value. The results shown in Table 2 demonstrate that roughly uniform optical properties can be obtained without any dependence on the type of plasticizer used

TABLE 2

| | Plasticizer | Thickness of Intermediate Film (mm) | Transmission (%) near 583 nm | | |
|---|---|---|---|---|---|
| | | | Base | Peak | Peak Size |
| Example 1 | 3GO | 0.75 | 89.1 | 59.8 | 29.3 |
| Example 2 | DBP | 0.80 | 87.2 | 57.0 | 30.2 |
| Example 3 | BBP | 0.75 | 87.4 | 56.7 | 30.7 |
| Example 4 | TCP | 0.80 | 86.2 | 57.0 | 29.2 |
| Comparative Example 1 | 3GO | 0.75 | 86.7 | — | — |

TABLE 2-continued

| | Plasticizer | Thickness of Intermediate Film (mm) | Transmission (%) near 583 nm | | |
|---|---|---|---|---|---|
| | | | Base | Peak | Peak Size |

3GO: triethylene glycol bis(2-ethylhexanoate)
DBP: dibutylphthalate
BBP: benzylbutylphthalate
TCP: tricresyl phosphate

Example 5

50 parts by weight of the triethylene glycol bis(2-ethylhexanoate) solution of a mixed neodymium salt (m=1, m=2) of monoisobutylphthalic acid-isobutyric acid obtained in Dissolution Example 3 was mixed with 100 parts by weight of polyvinyl butyral "BH-3", and a laminated glass was prepared in the same manner as in Example 1. This laminated glass was a transparent material of the same tone but slightly lighter than that of Example 1.

Dissolution Example 5 and Example 6

Dissolution Example 5

2.00 g of the neodymium salt of mono(n-butyl)phthalic acid prepared in the above Synthesis Example 5 and 2.00 g of the neodymium salt of isobutyric acid prepared in the above Synthesis Example 3 were added and mixed into 20 ml of dichloromethane in a 50 ml screw bottle, a magnetic stirrer was used to stir while heating to 35° C., and the slurry was observed to dissolve after 2 hours. 20.00 g of triethylene glycol di-2-ethylhexanoate were mixed into this transparent solution, to obtain a uniform transparent liquid. This solution was manipulated in the same way as in Dissolution Example 1 to distill the dichloromethane. The solution with the dichloromethane removed was a uniform transparent liquid.

Example 6

Next, 50 parts by weight of this solution were mixed into 100 parts by weight of polyvinyl butyral "BH-3", and this mixture was roll-kneaded and hot/cold pressed like Example 1 to prepare a transparent plasticized polyvinyl butyral resin sheet about 1 mm thick, i.e. an intermediate film for use in laminated glass.

This intermediate sheet was sandwiched between two 60 mm×60 mm glass sheets with a thickness of 1.3 mm and manipulated in the same manner as Example 1, to prepare a laminated glass. This laminated glass was a transparent material having a blue-violet tone like Example 1, and had a visible-UV spectrum similar to FIG. 1.

Dissolution Example 6 and Example 7

Dissolution Example 6

5.00 g of the neodymium salt of mono(2-phenoxyethyl) phthalic acid prepared in the above Synthesis Example 6 and 1.00 g of the neodymium salt of isobutyric acid prepared in Synthesis Example 3 were added and mixed into 20 ml of dichloromethane in a 50 ml screw bottle, a magnetic stirrer was used to stir, and the slurry was observed to dissolve promptly at room temperature (25° C.). 20.00 g of triethylene glycol di-2-ethylhexanoate were mixed into this transparent solution, to obtain a uniform transparent liquid. This solution was manipulated in the same way as in Dissolution Example 1 to distill the dichloromethane. The solution with the dichloromethane removed was a uniform transparent liquid.

Example 7

Next, 52 parts by weight of this solution were mixed into 100 parts by weight of polyvinyl butyral "BH-3", and this mixture was roll-kneaded and hot/cold pressed like Example 1 to prepare a transparent plasticized polyvinyl butyral resin sheet about 1 mm thick, i.e. an intermediate film for use in laminated glass.

This intermediate sheet was sandwiched between two 60 mm×60 mm glass sheets with a thickness of 1.3 mm and manipulated in the same manner as Example 1, to prepare a laminated glass. This laminated glass was a transparent material having a blue-violet tone like Example 1, and had a visible-UV spectrum similar to FIG. 1.

Dissolution Example 7 and Example 8

Dissolution Example 7

2.42 g of the neodymium salt of monoisobutylphthalic acid prepared in the above Synthesis Example 1 and 1.80 g of the neodymium salt of phenoxyacetic acid prepared in Synthesis Example 7 were added and mixed into 16 ml of dichloromethane in a 50 ml screw bottle, a magnetic stirrer was used to stir, and the slurry was observed to dissolve after 2 hours at room temperature (25° C.). 16.00 g of triethylene glycol di-2-ethylhexanoate were mixed into this transparent solution, to obtain a uniform transparent liquid. This solution was manipulated in the same way as in Dissolution Example 1 to distill the dichloromethane. The solution with the dichloromethane removed was a uniform transparent liquid.

Example 8

Next, 50.55 parts by weight of this solution were mixed into 100 parts by weight of polyvinyl butyral "BH-3", and this mixture was roll-kneaded and hot/cold pressed like Example 1 to prepare a transparent plasticized polyvinyl butyral resin sheet about 1 mm thick, i.e. an intermediate film for use in laminated glass.

This intermediate sheet was sandwiched between two 60 mm×60 mm glass sheets with a thickness of 1.3 mm and manipulated in the same manner as Example 1, to prepare a laminated glass. This laminated glass was a transparent material having a blue-violet tone like Example 1, and had a visible-UV spectrum similar to FIG. 1.

Dissolution Example 8 and Example 9

Dissolution Example 8

3.22 g of the neodymium salt of monoisobutylphthalic acid prepared in the above Synthesis Example 1 and 1.35 g of the neodymium salt of 4-tertiary-butylbenzoic acid prepared in Synthesis Example 8 were added and mixed into 16 ml of dichloromethane in a 50 ml screw bottle, a magnetic stirrer was used to stir, and the slurry was observed to dissolve after 5 minutes at room temperature (25° C.). 16.00 g of triethylene glycol di-2-ethylhexanoate were mixed into this transparent solution, to obtain a uniform transparent liquid. This solution was manipulated in the same way as in Dissolution Example 1 to distill the dichloromethane. The solution with the dichloromethane removed was a uniform transparent liquid.

Example 9

Next, 51.05 parts by weight of this solution were mixed into 100 parts by weight of polyvinyl butyral "BH-3", and this mixture was roll-kneaded and hot/cold pressed like Example 1 to prepare a transparent plasticized polyvinyl butyral resin sheet about 1 mm thick, i.e. an intermediate film for use in laminated glass.

This intermediate sheet was sandwiched between two 60 mm×60 mm glass sheets with a thickness of 1.3 mm and manipulated in the same manner as Example 1, to prepare a laminated glass. This laminated glass was a transparent material having a blue-violet tone like Example 1, and had a visible-UV spectrum similar to FIG. 1.

Dissolution Example 9 and Example 10

Dissolution Example 9

3.23 g of the neodymium salt of monoisobutylphthalic acid prepared in the above Synthesis Example 1 and 1.20 g of the neodymium salt of 2-methoxybenzoic acid prepared in Synthesis Example 9 were added and mixed into 16 ml of dichloromethane in a 50 ml screw bottle, a magnetic stirrer was used to stir, and the slurry was observed to dissolve after 10 minutes at room temperature (25° C.). 16.00 g of triethylene glycol di-2-ethylhexanoate were mixed into this transparent solution, to obtain a uniform transparent liquid. This solution was manipulated in the same way as in Dissolution Example 1 to distill the dichloromethane. The solution with the dichloromethane removed was a uniform transparent liquid.

Example 10

Next, 51.45 parts by weight of this solution were mixed into 100 parts by weight of polyvinyl butyral "BH-3", and this mixture was roll-kneaded and hot/cold pressed like Example 1 to prepare a transparent plasticized polyvinyl butyral resin sheet about 1 mm thick, i.e. an intermediate film for use in laminated glass.

This intermediate sheet was sandwiched between two 60 mm×60 mm glass sheets with a thickness of 1.3 mm and manipulated in the same manner as Example 1, to prepare a laminated glass. This laminated glass was a transparent material having a blue-violet tone like Example 1, and had a visible-UV spectrum similar to FIG. 1.

Dissolution Example 10 and Example 11

Dissolution Example 10

2.42 g of the neodymium salt of monoisobutylphthalic acid prepared in the above Synthesis Example 1 and 3.00 g of the neodymium salt of mono(2-phenoxyethyl)phthalic acid prepared in Synthesis Example 6 were added to 16.00 g of triethylene glycol di-2-ethylhexanoate, and heated to 60° C. while stirring with a magnetic stirrer, to obtain a uniform transparent solution 1 hour later.

Example 11

Next, 53.58 parts by weight of this solution were mixed into 100 parts by weight of polyvinyl butyral "BH-3", and this mixture was roll-kneaded and hot/cold pressed like Example 1 to prepare a transparent plasticized polyvinyl butyral resin sheet about 1 mm thick, i.e. an intermediate film for use in laminated glass.

This intermediate sheet was sandwiched between two 60 mm×60 mm glass sheets with a thickness of 1.3 mm and manipulated in the same manner as Example 1, to prepare a laminated glass. This laminated glass was a transparent material having a blue-violet tone like Example 1, and had a visible-UV spectrum similar to FIG. 1.

Example 12

7.00 g of a neodymium salt of mono(2-butoxyethyl)phthalic acid as prepared in the above Synthesis Example 10 were added and mixed into 20 ml of dichloromethane, to promptly obtain a transparent solution. 20.00 g of triethylene glycol di-2-ethylhexanoate were added and mixed with this solution, to obtain a uniform transparent liquid. This solution was manipulated in the same manner as Dissolution Example 1, to distill the dichloromethane. The solution with the dichloromethane removed was a uniform transparent liquid. Next, 54.00 parts by weight of this solution were mixed into 100 parts by weight of polyvinyl butyral "BH-3", and this mixture was roll-kneaded and hot/cold pressed like Example 1 to prepare a transparent plasticized polyvinyl butyral resin sheet about 1 mm thick, i.e. an intermediate film for use in laminated glass.

This intermediate sheet was sandwiched between two 60 mm×60 mm glass sheets with a thickness of 1.3 mm and manipulated in the same manner as Example 1, to prepare a laminated glass. This laminated glass was a transparent material having a blue-violet tone like Example 1, and had a visible-UV spectrum similar to FIG. 1.

The proportional contents of the mixed neodymium salts, polyvinyl butyral and plasticizer used in the preparation of the intermediate films described in the above Examples 1 and 6-12 are shown below

The invention claimed is:

1. An intermediate film for use in laminated glass, comprising a resin composition containing polyvinyl butyral, a plasticizer and a neodymium compound soluble in said plasticizer, wherein the neodymium compound is a neodymium salt of a polyvalent ester of a dicarboxylic or polycarboxylic acid wherein one carboxyl group is not esterified.

2. An intermediate film in accordance with claim 1, wherein the neodymium salt of a polyvalent ester of a dicarboxylic or polycarboxylic acid wherein one carboxyl group is not esterified is represented by the following formula (1):

$$[(R_1OCO)_xR_2COO]_m(R_3COO)_nNd \quad (1)$$

wherein
R$_1$ represents an alkyl group or an aryl group,
R$_2$ represents an alkylene group or an arylene group,
R$_3$ represents a saturated or unsaturated alkyl group or aryl group, or a (R'$_1$OXO)$_x$R'$_2$ group (where R'$_1$ and R'$_2$ are defined the same as R$_1$ and R$_2$ except that R$_1$≠R'$_1$ and R$_2$≠R'$_2$),
x is an integer from 1-3, and
m is a positive number satisfying the relationship 0<m<3, and n is a number satisfying the relationship m+n=3.

3. An intermediate film in accordance with claim 2, wherein the neodymium salt of a polyvalent ester of a dicarboxylic or polycarboxylic acid wherein one carboxyl group is not esterified is a neodymium salt of at least two polyvalent ester monocarboxylic acids.

TABLE 3

| | Combination of Nd Salts | | | Composition of 3GO Solution of Nd Salt (g) | | | Composition of Intermediate Film (parts by weight) | | | Nd Salt Ratio: Moles per 100 g BH-3 |
|---|---|---|---|---|---|---|---|---|---|---|
| | Nd Salt of Form. (2) | Nd Salt of Form. (3) (R$_3$=R'$_1$OCO$_x$R'$_2$ group) | Molar Ratio | Former | Latter | 3GO | BH-3 | 3GO | Nd salt | |
| Example 1 | NIBP | NIBA | 2/1 | 6.00 | 1.50 | 20.00 | 100 | 40 | 15.00 | 0.0223 |
| Example 6 | NBP | NIBA | 1/2 | 2.00 | 2.00 | 20.00 | 100 | 40 | 8.00 | 0.0148 |
| Example 7 | NPOEP | NIBA | 2/1 | 5.00 | 1.00 | 20.00 | 100 | 40 | 12.00 | 0.0149 |
| Example 8 | NIBP | NPOAA | 1.5/1.5 | 2.42 | 1.80 | 16.00 | 100 | 40 | 10.55 | 0.0150 |
| Example 9 | NIBP | NTTB | 2/1 | 3.22 | 1.35 | 16.00 | 100 | 40 | 11.05 | 0.0150 |
| Example 10 | NIBP | NOMOB | 2/1 | 3.23 | 1.20 | 16.00 | 100 | 40 | 11.45 | 0.0150 |
| | Nd salt of Form. (2) | Nd salt of Form. (3) (R$_3$=R'$_1$OCO$_x$R'$_2$ group) | | | | | | | | |
| Example 11 | NIBP | NPOEP | 1.5/1.5 | 2.42 | 3.00 | 16.00 | 100 | 40 | 13.58 | 0.0150 |
| Example 12 | NBEP | — | — | 7.00 | — | 20.00 | 100 | 40 | 14.00 | 0.0149 |

NIBP: Nd(CH$_3$CH(CH$_3$)CH$_2$OCOΦCOO—)$_3$, Fw = 807.8, Nd salt of phthalic acid mono(isobutyl)ester
NIBA: Nd(CH$_3$CH(CH$_3$)COO—)$_3$, Fw = 405.5, Nd salt of isobutyric acid
NBP: Nd(CH$_3$CH$_2$CH$_2$CH$_2$OCOΦCOO—)$_3$, Fw = 807.8, Nd salt of phthalic acid mono(n-butyl)ester
NPOEP: Nd(ΦOCH$_2$CH$_2$OCOΦCOO—)$_3$, Fw = 1000.1, Nd salt of phthalic acid mono(2-phenoxyethyl)ester
NPOAA: Nd(ΦOCH$_2$COO—)$_3$, Fw = 597.7, Nd salt of phenoxyacetic acid
NTTB: Nd((CH$_3$)$_3$CΦCOO—)$_3$, Fw = 675.7, Nd salt of 4-(t-butyl)benzoic acid
NOMOB: Nd(CH$_3$OΦCOO—)$_3$, Fw = 597.7, Nd salt of 2-methoxybenzoic acid
NBEP: Nd(CH$_3$CH$_2$CH$_2$CH$_2$OCH$_2$CH$_2$OCOΦCOO—)$_3$, Fw = 940.1, Nd salt of phthalic acid mono(n-butoxyethyl)ester
3GO: Triethylene glycol di(2-ethylhexanoate)
BH-3: Polyvinyl butyral 4. An intermediate film in accordance with any one of claim 1, 2 or 3, wherein said resin composition contains 100 parts by weight of polyvinyl butyral, 20-100 parts by weight of the plasticizer and 1-40 parts by weight of the neodymium salt of the polyvalent ester of a dicarboxylic or polycarboxylic acid wherein one carboxyl group is not esterified.

5. A laminated glass characterized by being formed by sandwiching an intermediate film in accordance with any one of claims 1, 2 or 3 between a pair of glass panels.

6. A neodymium salt of a polyvalent ester monocarboxylic acid represented by the following formula (1):

$$[(R_1OCO)_xR_2COO]_m(R_3COO)_nNd \qquad (1)$$

wherein
   $R_1$ represents an alkyl group or an aryl group,
   $R_2$ represents an alkylene group or an arylene group,
   $R_3$ represents a saturated or unsaturated alkyl group or aryl group, or a $(R'_1OCO)_xR'_2$ group (where $R'_1$ and $R'_2$ are defined the same as $R_1$ and $R_2$ except that $R_1 \neq R'_1$ and $R_2 \neq R'_2$).
   x is an integer from 1-3, and
   m is a positive number satisfying the relationship $0<m<3$, and n is a number satisfying the relationship $m+n=3$.

7. A neodymium salt of a polyvalent ester monocarboxylic acid characterized by being obtained by mixing at least one polyvalent ester monocarboxylic acid or a neodymium salt thereof expressed by the following Formula (2):

$$(R_1OCO)_xR_2COOH \qquad (2)$$

wherein
   $R_1$ represents an alkyl group or an aryl group, $R_2$ represents an alkylene group or an arylene group and x is an integer of 1-3; and
   at least one aliphatic or aromatic monocarboxylic acid or a neodymium salt thereof, or at least one polyvalent ester monocarboxylic acid or a neodymium salt thereof expressed by the following Formula (3):

$$R_3COOH \qquad (3)$$

wherein
   $R_3$ represents a saturated or unsaturated alkyl group or aryl group, or a $(R'_1OCO)_xR'_2$ group where $R'_1$ and $R'_2$ are defined the same as $R_1$ and $R_2$ except that $R_1 \neq R'_1$ and $R_2 \neq R'_2$; or
   when mixing carboxylic acids of the above Formulas (2) and (3), further mixing in a neodymium compound and allowing to react.

8. A neodymium salt of a polyvalent ester monocarboxylic acid in accordance with claim 7, wherein $R_3$ is not a $(R'_1OCO)_xR'_2$ group.

9. A neodymium salt of a polyvalent ester monocarboxylic acid in accordance with claim 7, wherein $R_3$ is a $(R'_1OCO)_xR'_2$ group.

10. A method of producing a neodymium salt of a polyvalent ester monocarboxylic acid, characterized by mixing at least one polyvalent ester monocarboxylic acid or a neodymium salt thereof expressed by the following Formula (2):

$$(R_1OCO)_xR_2COOH \qquad (2)$$

wherein
   $R_1$ represents an alkyl group or an aryl group, $R_2$ represents an alkylene group or an arylene group and x is an integer of 1-3; and
   at least one aliphatic or aromatic monocarboxylic acid or a neodymium salt thereof, or at least one polyvalent ester monocarboxylic acid or a neodymium salt thereof expressed by the following Formula (3):

$$R_3COOH \qquad (3)$$

wherein
   $R_3$ represents a saturated or unsaturated alkyl group or aryl group, or a $(R'_1OCO)_xR'_2$ group where $R'_1$ and $R'_2$ are defined the same as $R_1$ and $R_2$ except that $R_1 \neq R'_1$ and $R_2 \neq R'_2$; or
   when mixing carboxylic acids of the above Formulas (2) and (3), further mixing in a neodymium compound and allowing to react.

11. A method of producing a neodymium salt of a polyvalent ester monocarboxylic acid in accordance with claim 10, wherein $R_3$ is not a $(R'_1OCO)_xR'_2$ group.

12. A method of producing a neodymium salt of a polyvalent ester monocarboxylic acid in accordance with claim 10, wherein $R_3$ is a $(R'_1OCO)_xR'_2$ group.

* * * * *